United States Patent [19]
Guillou-Bonnici et al.

[11] Patent Number: 5,744,308
[45] Date of Patent: Apr. 28, 1998

[54] CHIMERA OLIGONUCLEOTIDE AND ITS UTILIZATION FOR OBTAINING TRANSCRIPTS OF A NUCLEIC ACID

[75] Inventors: Françoise Guillou-Bonnici, Villeurbanne; Philippe Cleuziat, Lyons; François Mallet, Villeurbanne, all of France; Pierre Levasseur, Watertown, Mass.; William McAllister, Edison, N.J.

[73] Assignee: Bio Merieux, Marcy l'Etoile, France

[21] Appl. No.: 533,912

[22] Filed: Sep. 26, 1995

[30] Foreign Application Priority Data

Sep. 26, 1994 [FR] France .................. 94 11455

[51] Int. Cl.$^6$ .............. C12Q 1/68; C12P 19/34
[52] U.S. Cl. ................. 435/6; 435/91.2
[58] Field of Search ................ 435/6, 5, 91.1, 435/91.2; 935/77, 78

[56] References Cited

U.S. PATENT DOCUMENTS

| | | | |
|---|---|---|---|
| 5,169,766 | 12/1992 | Schuster et al. | 435/6 |
| 5,194,370 | 3/1993 | Berninger et al. | 435/6 |
| 5,437,990 | 8/1995 | Burg et al. | 435/91.2 |

FOREIGN PATENT DOCUMENTS

| | | |
|---|---|---|
| 0 329 822 | 8/1989 | European Pat. Off. |
| 0 369 775 | 5/1990 | European Pat. Off. |
| 0 373 960 | 6/1990 | European Pat. Off. |
| 0 500 224 | 8/1992 | European Pat. Off. |
| 0 587 298 | 3/1994 | European Pat. Off. |
| 88/10315 | 12/1988 | WIPO |
| 89/06700 | 7/1989 | WIPO |
| 90/06995 | 6/1990 | WIPO |
| 91/02818 | 3/1991 | WIPO |
| 92/22663 | 12/1992 | WIPO |

OTHER PUBLICATIONS

Richard D. Abramson et al., "Nucleic Acid Amplification Technologies", *Current Opinion in Biotechnology*, pp. 41–47, May 14, 1993.

G. R. Davis et al., "Detection of Human Immunodeficiency Virus Type 1 in AIDS Patients Using Amplification–Mediated Hybridization Analyses: Reproducibility and Quantitative Limitations", *Journal of Infectious Diseases*, vol. 162, pp. 13–20, 1990.

N.D. Sinha et al., "Labile Exocyclic Amine Protection of Nucleosides in DNA, RNA and Oligonucleotide Analog Synthesis Facilitating N–Deacylation, Minimizing Depurination and Chain Degradation", *Biochimie*, vol. 75, pp. 13–23, 1993.

Ricki Lewis, "PCR's Competitors are Alive and Well and Moving Rapidly Towards Commercialization", *Genetic Engineering News*, vol. 12, No. 9, pp. 1, 8–9, Jun. 1, 1992.

J.C. Guatelli et al., "Isothermal, In Vitro Amplification of Nucleic Acids by a Multienzyme Reaction Modeled After Retroviral Replication", *Proceedings of the National Academy of Sciences, USA*, vol. 87, No. 5, Mar. 1990, pp. 1874–1878.

T. Kievits et al., "NASBA Isothermal Enzymatic In Vitro Nucleic Acid Amplification Optimized for the Diagnosis of HIV–1 Infection", *Journal of Virological Methods*, vol. 35, 1991, pp. 273–286.

*Primary Examiner*—Eggerton A. Campbell
*Attorney, Agent, or Firm*—Oliff & Berridge, P.L.C.

[57] ABSTRACT

A chimera oligonucleotide is provided that can be used in a process for obtaining transcripts and/or amplification of a target sequence of a nucleic acid, having, at its 3' end, a downstream sequence. The oligonucleotide comprises successively, from 5' to 3', 1) a first oligonucleotide segment, of the DNA type, comprising a sense sequence of a promoter of an RNA polymerase, 2) a second oligonucleotide segment, of the DNA type, capable of hybridizing with the downstream sequence, and 3) a third oligonucleotide segment, of the RNA type, capable of hybridizing with a part of the target sequence contiguous to the downstream sequence, the third segment being blocked at 3'. A process using the chimera oligonucleotide and an enzyme system containing DNA polymerase activity, RNA polymerase activity, and a third activity, for example, an RNase H activity provides transcription products of the target. By adding a second chimera oligonucleotide capable of hybridizing with the complement of the target, cyclic amplification of the target and its complement are obtained.

9 Claims, 1 Drawing Sheet

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:1:

TATTAACCCT CACTAAA                17

( 2 ) INFORMATION FOR SEQ ID NO:2:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:2:

TAATACGACT CACTATA                17

( 2 ) INFORMATION FOR SEQ ID NO:3:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:3:

ATTTAGGTGA CACTATA                17

( 2 ) INFORMATION FOR SEQ ID NO:4:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:4:

AATTAGGGCA CACTATA                17

( 2 ) INFORMATION FOR SEQ ID NO:5:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear -continued ( i i ) MOLECULE TYPE: other nucleic acid
    ( A ) DESCRIPTION: /desc = "DNA"

( x i ) SEQUENCE DESCRIPTION: SEQ ID NO:5:

TAATACGACT CACTAAT      17

( 2 ) INFORMATION FOR SEQ ID NO:6:

( i ) SEQUENCE CHARACTERISTICS:
    ( A ) LENGTH: 6 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:6:

GGGAGA      6

( 2 ) INFORMATION FOR SEQ ID NO:7:

( i ) SEQUENCE CHARACTERISTICS:
    ( A ) LENGTH: 6 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:7:

GAAGGG      6

( 2 ) INFORMATION FOR SEQ ID NO:8:

( i ) SEQUENCE CHARACTERISTICS:
    ( A ) LENGTH: 6 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:8:

GCGAGA      6

( 2 ) INFORMATION FOR SEQ ID NO:9:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "RNA"

( x i ) SEQUENCE DESCRIPTION: SEQ ID NO:9:

UGCCAUAACC AUGAGUG      17

( 2 ) INFORMATION FOR SEQ ID NO:10:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:10:

TGCCATAACC ATGAGTG                                                                      17

( 2 ) INFORMATION FOR SEQ ID NO:11:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "3'DNA BLOCKED, C3NH2"

( x i ) SEQUENCE DESCRIPTION: SEQ ID NO:11:

TAATACGACT CACTATAGGG TTGGCCGCAG TGTTCACTCA TGGTTATGGC                                   50

( 2 ) INFORMATION FOR SEQ ID NO:12:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "3'DNA BLOCKED, C3NH2"

( x i ) SEQUENCE DESCRIPTION: SEQ ID NO:12:

TAATACGACT CACTATAG                                                                     18

( 2 ) INFORMATION FOR SEQ ID NO:13:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "3'BLOCKED, C3NH2"

( x i ) SEQUENCE DESCRIPTION: SEQ ID NO:13:

ATTTAGGTGA CACTATAGAA GTTGGCCGCA GTGTTCACTC ATGGTTATGG C                                 51

( 2 ) INFORMATION FOR SEQ ID NO:14:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "3'BLOCKED, C3NH2"

( x i ) SEQUENCE DESCRIPTION: SEQ ID NO:14:

ATTTAGGTGA CACTATAG                                                                     18

( 2 ) INFORMATION FOR SEQ ID NO:15:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: other nucleic acid
     ( A ) DESCRIPTION: /desc = "3'BLOCKED, C3NH2"

( x i ) SEQUENCE DESCRIPTION: SEQ ID NO:15:

AATTAACCCT CACTAAAGGG TTGGCCGCAG TGTTCACTCA TGGTTATGGC    50

( 2 ) INFORMATION FOR SEQ ID NO:16:

( i ) SEQUENCE CHARACTERISTICS:
          ( A ) LENGTH: 18 bases
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc = "3'BLOCKED, C3NH2"

( x i ) SEQUENCE DESCRIPTION: SEQ ID NO:16:

AATTAACCCT CACTAAAG    18

( 2 ) INFORMATION FOR SEQ ID NO:17:

( i ) SEQUENCE CHARACTERISTICS:
          ( A ) LENGTH: 51 bases
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc = "DNA"

( x i ) SEQUENCE DESCRIPTION: SEQ ID NO:17:

GCCATAACCA TGAGTGAACA CTGCGGCCAA CTTCTATAGT GTCACCTAAA T    51

( 2 ) INFORMATION FOR SEQ ID NO:18:

( i ) SEQUENCE CHARACTERISTICS:
          ( A ) LENGTH: 50 bases
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc = "DNA"

( x i ) SEQUENCE DESCRIPTION: SEQ ID NO:18:

GCCATAACCA TGAGTGAACA CTGCGGCCAA CCCTATAGTG AGTCGTATTA    50

( 2 ) INFORMATION FOR SEQ ID NO:19:

( i ) SEQUENCE CHARACTERISTICS:
          ( A ) LENGTH: 50 bases
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc = "DNA"

( x i ) SEQUENCE DESCRIPTION: SEQ ID NO:19:

GCCATAACCA TGAGTGAACA CTGCGGCCAA CCCTTTAGTG AGGGTTAATT    50

( 2 ) INFORMATION FOR SEQ ID NO:20:

( i ) SEQUENCE CHARACTERISTICS:
          ( A ) LENGTH: 16 bases
          ( B ) TYPE: nucleic acid
          ( C ) STRANDEDNESS: single
          ( D ) TOPOLOGY: linear ( i i ) MOLECULE TYPE: other nucleic acid
    ( A ) DESCRIPTION: /desc = "RNA"

( x i ) SEQUENCE DESCRIPTION: SEQ ID NO:20:

GCCAUAACCA UGAGUG    16

( 2 ) INFORMATION FOR SEQ ID NO:21:

( i ) SEQUENCE CHARACTERISTICS:
    ( A ) LENGTH: 34 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:21:

AACACTGCGG CCAACCCTTT AGTGAGGGTT AATT    34

( 2 ) INFORMATION FOR SEQ ID NO:22:

( i ) SEQUENCE CHARACTERISTICS:
    ( A ) LENGTH: 35 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:22:

AACACTGCGG CCAACCCTAT AGTGAGTCGT ATTAA    35

( 2 ) INFORMATION FOR SEQ ID NO:23:

( i ) SEQUENCE CHARACTERISTICS:
    ( A ) LENGTH: 33 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "RNA"

( x i ) SEQUENCE DESCRIPTION: SEQ ID NO:23:

GCCAUAACCA UGAGUGAACA CUGCGGCCAA CCC    33

( 2 ) INFORMATION FOR SEQ ID NO:24:

( i ) SEQUENCE CHARACTERISTICS:
    ( A ) LENGTH: 34 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "RNA"

( x i ) SEQUENCE DESCRIPTION: SEQ ID NO:24:

AGAGAAUUAU GCAGUGCUGC CAUAACCAUG AGUG    34

( 2 ) INFORMATION FOR SEQ ID NO:25:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:25:

AGAGAATTAT GCAGTGC      17

( 2 ) INFORMATION FOR SEQ ID NO:26:

( i ) SEQUENCE CHARACTERISTICS:
    ( A ) LENGTH: 16 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:26:

TACTGTCATG CCATCC      16

( 2 ) INFORMATION FOR SEQ ID NO:27:

( i ) SEQUENCE CHARACTERISTICS:
    ( A ) LENGTH: 57 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:27:

AAGTAAGTTG GCCGCAGTGT TATCACTCAT GGTTATGGCA GCACTGCATA ATTCTCT      57

( 2 ) INFORMATION FOR SEQ ID NO:28:

( i ) SEQUENCE CHARACTERISTICS:
    ( A ) LENGTH: 51 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:28:

TAATACGACT CACTATAGGG ATGGCATGAC AGTAAGAGAA TTATGCAGTG C      51

( 2 ) INFORMATION FOR SEQ ID NO:29:

( i ) SEQUENCE CHARACTERISTICS:
    ( A ) LENGTH: 29 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:29:

TAATACGACT CACTATAGGG CATGACAGT      29

( 2 ) INFORMATION FOR SEQ ID NO:30:

( i ) SEQUENCE CHARACTERISTICS:
    ( A ) LENGTH: 30 bases
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:30:

TAATACGACT CACTATAGGG CAGTGTTATC     30

( 2 ) INFORMATION FOR SEQ ID NO:31:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "RNA"

( x i ) SEQUENCE DESCRIPTION: SEQ ID NO:31:

AGAGAAUUAU GCAGUGCUGC CAUAACCAUG AGUGAUAACA CUGCGGCCAA C     51

( 2 ) INFORMATION FOR SEQ ID NO:32:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:32:

GCACTGCATA ATTCTT     16

( 2 ) INFORMATION FOR SEQ ID NO:33:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "5'AMINOLINK 2"

( x i ) SEQUENCE DESCRIPTION: SEQ ID NO:33:

CACTCATGGT TATGGCA     17

( 2 ) INFORMATION FOR SEQ ID NO:34:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:34:

TAATTCGACT CACTATAGGG GTCCTCCGAT CGTT     34

( 2 ) INFORMATION FOR SEQ ID NO:35:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:35:

TAATACGACT CACTATAGGG TTACGGATGG CATG                                34

( 2 ) INFORMATION FOR SEQ ID NO:36:

( i ) SEQUENCE CHARACTERISTICS:
      ( A ) LENGTH: 102 bases
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "RNA"

( x i ) SEQUENCE DESCRIPTION: SEQ ID NO:36:

GGGUUACGGA UGGCAUGACA GUAAGAGAAU UAUGCAGUGC UGCCAUAACC AUGAGUGAUA    60

ACACUGCGGC CAACUUACUU CUGACAACGA UCGGAGGACC CC                      102

( 2 ) INFORMATION FOR SEQ ID NO:37:

( i ) SEQUENCE CHARACTERISTICS:
      ( A ) LENGTH: 102 bases
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "RNA"

( x i ) SEQUENCE DESCRIPTION: SEQ ID NO:37:

GGGGUCCUCC GAUCGUUGUC AGAAGUAAGU UGGCCGCAGU GUUAUCACUC AUGGUUAUGG    60

CAGCACUGCA UAAUUCUCUU ACUGUCAUGC CAUCCGUAAC CC                      102

( 2 ) INFORMATION FOR SEQ ID NO:38:

( i ) SEQUENCE CHARACTERISTICS:
      ( A ) LENGTH: 16 bases
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "5'AMINOLINK 2"

( x i ) SEQUENCE DESCRIPTION: SEQ ID NO:38:

GGATGGCATG ACAGTA                                                    16

( 2 ) INFORMATION FOR SEQ ID NO:39:

( i ) SEQUENCE CHARACTERISTICS:
      ( A ) LENGTH: 17 bases
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "5'AMINOLINK 2"

( x i ) SEQUENCE DESCRIPTION: SEQ ID NO:39:

GTTGGCCGCA GTGTTAT                                                   17

( 2 ) INFORMATION FOR SEQ ID NO:40:

( i ) SEQUENCE CHARACTERISTICS:
      ( A ) LENGTH: 35 bases ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:40:

AACACTGCGG CCAACTTCTA TAGTGTCACC TAAAT        35

( 2 ) INFORMATION FOR SEQ ID NO:41:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:41:

TTTAGTGAGG GTTAATT        17

( 2 ) INFORMATION FOR SEQ ID NO:42:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "RNA"

( x i ) SEQUENCE DESCRIPTION: SEQ ID NO:42:

AAGAGAAUUA UGCAGCA        17

( 2 ) INFORMATION FOR SEQ ID NO:43:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "RNA"

( x i ) SEQUENCE DESCRIPTION: SEQ ID NO:43:

ACUCAUGGUU AUGGCUA        17

( 2 ) INFORMATION FOR SEQ ID NO:44:

( i ) SEQUENCE CHARACTERISTICS:
( A ) LENGTH: 16 bases
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "RNA"

( x i ) SEQUENCE DESCRIPTION: SEQ ID NO:44:

GUCAGAAGUA AGUUGC        16

( 2 ) INFORMATION FOR SEQ ID NO:45:

( i ) SEQUENCE CHARACTERISTICS:
( A ) LENGTH: 17 bases ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "RNA"

( x i ) SEQUENCE DESCRIPTION: SEQ ID NO:45:

ACAGUAAGAG AAUUACC                       17

CHIMERA OLIGONUCLEOTIDE AND ITS UTILIZATION FOR OBTAINING TRANSCRIPTS OF A NUCLEIC ACID

BACKGROUND OF THE INVENTION

The present invention relates to novel chimera oligonucleotides allowing transcription and amplification of target nucleic acid sequences as well as a process for amplification of nucleic acids by transcription.

In technologies relating to nucleic acids and genetic material, it is often necessary to determine whether a gene, a part of a gene, or a nucleotide sequence is present in a living organism, a cell extract from this organism, or any other biological sample.

The usefulness of research into specific nucleotide sequences is enormous, particularly for detection of pathogenic organisms, determination of the presence of alleles, detection of the presence of lesions in a host genome, and detection of a particular mRNA or modification of a cell host. Genetic diseases such as Huntington's disease, muscular dystrophy, phenylketonuria, and β-thalassemia can be diagnosed by analyzing the DNA of individuals. Moreover, diagnosis or identification of viruses, viroids, bacteria, fungi, protozoans, or any other form of plant or animal life can be carried out by hybridization experiments with nucleic probes.

Various types of nucleic acid detection methods are described in the literature. These methods, particularly those requiring detection of polynucleotides, are based on the pairing properties of complementary strands of nucleic acids in the DNA-DNA, DNA-RNA, and RNA-RNA duplexes by formation of hydrogen bonds between the adenine and thymine bases (A-T) and the guanine and cytosine bases (G-C) of double-stranded DNA or between the adenine and uracil bases (A-U) in the DNA-RNA or RNA-RNA duplexes. Pairing of nucleic acid strands is usually called "nucleic acid hybridization" or simply "hybridization."

In the various examples cited above, after identifying a sequence specific to an organism or a disease, nucleic acids need to be extracted from a sample and a determination made as to whether this sequence (also called "target") is present. Numerous methods of detection have been developed with this in view.

For implementation of the invention, it is generally necessary for one or more specific sequences of the target to have previously been identified. The most direct method for detecting the presence of a target sequence in a nucleic acid sample is to obtain a "probe" whose sequence is sufficiently complementary to a part of the target nucleic acid to hybridize therewith. Thus synthesized, the probe can be placed in the presence of a sample containing nucleic acids and, if the target sequence is present, the probe will hybridize and form a reaction product. In the absence of a target sequence, avoiding any nonspecific hybridization phenomenon, no reaction product will form. If the synthesized probe is coupled with a detectable marker, the reaction product can be detected by measuring the quantity of marker present. Transfers of the Southern type (Southern E. M., *J. Mol. Biol.*, 98, 503 (1975) or Northern type or the Dot blot or sandwich hybridization technique (Dunn A. R. and Hassel *J. A., Cell*, 12, 23, (1977) are examples of methods that can be used.

The main difficulty with this approach, however, is that it is not directly applicable to the case where the number of copies of the target sequence present in a sample is small (i.e. less than $10^7$). Under these conditions it is difficult to distinguish a significant signal larger than the background noise of the reaction (namely to distinguish the specific attachment of a probe to its target sequence from nonspecific attachment between the probe and a different sequence of the target sequence). One of the solutions to this problem is to increase the detection signal by a supplementary reaction.

Consequently, a number of methods for increasing the detection power of these hybridization techniques have been described. These methods, known as "amplification methods," can be divided into three categories: target amplification, probe amplification, and signal amplification. The articles by Lewis (1992, *Genetic Engineering News*, 12:1–9) and by Abramson and Myers (1993, *Curr. Opin. Biotechnol.*, 4:41–47) are good general surveys of these methods.

Target amplification consists of specifically multiplying a nucleic acid fragment present in a sample. It considerably increases the number of copies of a target nucleic sequence to be detected.

The target amplification techniques described in the literature are based mainly either on repetition of DNA synthesis cycles in vitro, by elongating hybridized nucleotide primers on the target sequence to be amplified by a DNA polymerase (polymerase chain amplification method known as PCR: see U.S. Pat. Nos. 4,683,195, 4,683,202 and 4,800,159; European Patent No. 0 201 184; the method known as repair chain reaction or RCR: see patent application No. WO 90/01069; the strand displacement amplification (SDA) method: see European Patent No. 0 497 272; the exonuclease-mediated strand displacement amplification method: see European Patent No. 0 500 224), or repetition of RNA synthesis cycles in vitro by a transcription reaction using an RNA polymerase.

Several of these target amplification methods based on transcript amplification have been described. The method known as the TAS method, described in Patent Application No. WO 88/10315, consists in repeating a three-step cycle. The first step synthesizes a cDNA from an RNA in the presence of a reverse transcriptase and a deoxynucleotide primer containing a specific sequence of phage polymerase RNA promoter. Following thermal denaturation of the RNA/cDNA heteroduplex, the single-stranded strand of cDNA is replicated by the reverse transcriptase in the presence of an antisense oligonucleotide primer. The DNA homoduplex thus obtained in this second step contains a double-stranded promoter to which a phage DNA-dependent RNA polymerase can attach. The third step is transcription, leading to 30 to 1000 molecules of RNA being obtained per template, and these molecules can then serve as a template for cDNA synthesis, thus continuing the amplification cycle (Davis et al., 1990, *J. Infect. Dis.*, 162:13–20).

There are various methods derived from TAS including self-sustained sequence replication (or 3SR) described in patent application WO 90/06995 and European Patent No. 0 373 960, the nucleic acid sequence-based amplification (NASBA) method described in patent application WO 91/02818 and European Patent No. 0 329 822, and the single primer sequence replication (SPSR) method described in U.S. Pat. No. 5,169,766. These methods have in common the combination of three enzyme activities: RNA- and DNA-dependent DNA polymerase (reverse transcriptase), ribonuclease H (RNase H; *Escherichia coli* enzyme and/or enzyme activity associated with reverse transcriptase), and DNA-dependent RNA polymerase (RNA polymerase from bacteriophage T7). These methods are based on the same principle and are carried out at a fixed temperature (between 37° and 45° C.) according to a continuous process of reverse transcription and transcription reactions to replicate an RNA target through the intermediary of cDNA. As in the case of TAS, an RNA polymerase fixation site (phage T7) is introduced into the cDNA by the primer used for the reverse transcription step. Nonetheless, denaturation of the RNA/cDNA heteroduplex is effected isothermally by specific hydrolysis of the RNA of this heteroduplex by RNase H activity. The free cDNA is then replicated from a second oligonucleotide primer by the reverse transcriptase. The DNA-DNA homoduplex is transcribed into RNA by RNA polymerase T7 and this RNA can in turn serve as a template for the next cycle.

Another method known as ligation-activated transcription (LAT) described in U.S. Pat. No. 5,194,370 uses the same enzyme activities as the three 3SR, SPSR, and NASBA methods and functions on the same cycle. It differs however by the manner in which a promoter sequence is installed: In this case it is introduced on the end of the cDNA by ligation of a rod-loop structure containing the promoter in the presence of a DNA ligase.

Other target amplification methods based on amplification of transcripts are described in European Patent Application No. 0 369 775. One differs from LAT only in the fact that the promoter is composed of two different oligonucleotides. The other uses two enzyme activities, one ligase and the other RNA-dependent RNA polymerase recognizing a double-stranded DNA promoter. The promoter, called a mobile promoter, is composed of two oligonucleotides. One has a sense promoter sequence and a probe sequence allowing hybridization on the 3' end of an RNA target and the other has only an antisense promoter sequence. By hybridization, the 5' end of the antisense promoter oligonucleotide is juxtaposed with the 3' end of the target then ligatured with this same end. Transcription by appropriate RNA polymerase results in synthesis of multiple transcripts. These transcripts are hybridized and ligatured to a second mobile promoter. Transcription of the RNA matrix results in synthesis of complementary transcripts. The process can be reiterated, leading to exponential amplification of the initial target sequence.

Target amplification methods can be replaced by probe amplification methods. The article by Birkenmeyer and Mushahwar (1991, *J. Virol. Meth.*, 35:117–126) surveys these methods. In the strict sense of the term they designate any process that leads to a large number of copies of the probe being obtained in vitro. One of them, the "Qβ replicase" method described in International Patent Application WO 87/06270 uses an RNA-dependent RNA polymerase, particularly that of the replicase from the Qβ phage. This enzyme has great specificity and affinity for the single-stranded RNA of this phage and can replicate this RNA in vitro (Biebricher et al., 1986, *Nature*, 321:98–91). The very long half-life of this enzyme allows synthesis of numerous complementary RNA strands corresponding to the positive and negative forms of this RNA molecule. Exploitation of this replication system is based on the possibility of inserting a probe within the RNA MDV-I, the natural substrate of Qβ replicase, without altering the effectiveness or specificity of its replication by the RNA polymerase of the Qβ phage (Lizardi et al. 1988, *BioTechnology*, 6:1197–1202). The amplification method consists of hybridizing the recombinant RNA probe on the target nucleic acid followed by intensive selective washing to eliminate any specific hybridization. The hybrid formed between the RNA probe and the target is then denatured and the RNA probe released is subjected to amplification by the Qβ replicase added in the middle.

Various detection techniques can be used for all the methods described above. One of them consists of detecting the reaction products with a specific size by electrophoretic separation. The methods vary according to the separation process which may involve separation on gel, or fixation on various solid phases (balls, microtitration plate, latex, or magnetic particles). Another method uses labeling of a detection probe with a radioisotope such as $^{32}P$, for example, then detecting the radioactivity emitted by the reaction products in combination (or not) with electrophoresis. Another method consists of chemically modifying an oligonucleotide primer by adding to it a ligand (biotin or digoxigenin for example), an enzyme (alkaline phosphatase, peroxidase, beta-galactosidase, for example), a fluorescent marker (phycobiliprotein, fluorescein, or rhodamine, for example), a luminescent marker (an acridinium ester, for example), electron density groups detectable by electron microscopy or electrical methods (conductivity, amperometry, voltametry, and impedance measurements for example), groups detectable by optical methods (diffraction, surface plasmon resonance, change in contact angle for example) or physical methods (atomic force spectroscopy, tunnel effect for example), or a combination of these modifications. Another method consists of developing a nucleotide detection primer which will hybridize on the amplification reaction product and will be extended by a polymerase in the presence of triphosphate ribonucleosides (this primer can in this case also be modified as described above). All these methods can be adapted to be operated either in a solid phase or in solution (homogeneous phase).

However, all the amplification techniques described above have at least one important limitation. They do not allow an amplification product to be obtained from a single type of target nucleic acid: RNA or DNA. In certain cases such as PCR, LCR, or RCR, the most limiting factor is the necessity of running several temperature cycles to dissociate the reaction products from the target. This limits the choice of usable enzymes to heat-stable enzymes. Moreover, running such successive temperature cycles is a constraint on automating these techniques. Another drawback to certain amplification techniques is the limitation in the size of the amplification reaction product. Techniques such as RCR or LCR allow only the target sequence corresponding to the primers and to the nucleotide probes used in the amplification process to be amplified. The nonspecific background noise (i.e. in the absence of the target) is also a serious drawback to certain techniques: In the case of LCR for example, ligation of the ends of the excess free oligonucleotides occurs even in the absence of the target. Other methods such as SDA are limited in the type of target sequence to be amplified since the target sequence must have no restriction site corresponding to the endonuclease used in the process so that it is essential to know the total nucleic acid sequence of the fragment to be amplified, or at least the restriction map of this fragment. This limitation is increased still further by the fact that the choice of restriction endonucleases is restricted to those able to restrict a recognition site comprising modified nucleotides. In addition to the limitations due to chemical synthesis, regarding the choice of modified nucleotide, the amplification process is also limited by its yield since it is known that the Km of the polymerases for modified nucleotides is greater than that for natural nucleotides for polymerases, hence the lower efficiency of incorporation of the modified nucleotides by the enzyme into the target to be amplified. Another drawback to certain amplification techniques resides in the high number of enzyme activities involved in the amplification process.

Methods derived from TAS such as 3SR or NASBA require at least four enzyme activities (DNA-dependent DNA polymerase, RNA-dependent DNA polymerase, DNA-dependent RNA polymerase, RNase H) or even five in the case of LAT (DNA ligase in addition). Hence it is very difficult to arrive at reaction conditions that simultaneously satisfy these four or five enzyme activities. Moreover, transcription techniques allow amplification only from RNA target molecules but not DNA. Finally, while various amplification techniques resort to nuclease activities (exonuclease, endonuclease, RNase) as the means of separating the nucleic acid strands (3SR, NASBA, European Patent No. 0 500 224), their use is nonetheless delicate since it is essential to obtain managed and strictly controlled action of these enzymes to maintain an equilibrium between the various enzyme activities involved.

In addition, currently known techniques of exponential amplification using RNA-dependent RNA polymerases have a far greater potential than other techniques since they use only one or two enzymes and do not require denaturation. However, these methods still have gaps. The Qβ replicase method does not allow direct amplification of the target because the specificity of the enzyme for its template is linked to a highly complex RNA structure which is difficult to install on a target. As for the mobile promoter method applied to an RNA template (described in Patent Application EP 0 369 775), it requires two oligonucleotides per ligation to be installed on the target with each cycle to form an operational promoter.

In view of the foregoing analysis, it appears desirable to design new amplification methods, and the present invention relates in particular to a method of cyclic amplification of a target nucleotide sequence with formation of transcripts, that is easy to implement, requires only two oligonucleotides, and can operate isothermally.

SUMMARY OF THE INVENTION

Before defining the invention more completely, we will provide hereinbelow the definition of some terms employed in the remainder of the specification.

The terms "nucleic acid fragment," "nucleic acid segment," and "oligonucleotide" are used without distinction in the present application to designate a DNA, RNA, or DNA/RNA chimera polynucleotide sequence which may contain one or more modified nucleotides. Such a polynucleotide sequence generally has a "length" of at least five deoxyribonucleotides and/or ribonucleotides which may contain at least one modified nucleotide. A modified polynucleotide sequence has for example at least one modified base such as inosine, 5-methyldeoxycytidine, 5-dimethylaminodeoxyuridine, deoxyuridine, 2,6-diaminopurine, 5-bromodeoxyuridine, pseudouridine, pseudoisocytidine, or any other modified base allowing hybridization to take place. The polynucleotide sequence can also be modified at the internucleotide bonds (which may for example involve phosphorothioate, H-phosphonate, or alkyl phosphonate bonds), or at the skeleton as in the case for example of alpha-oligonucleotides (French Patent No. 2,607,507) or PNAs (Egholm et al., 1992, *J. Am. Chem. Soc.*, 114:1895–1897). In one modified polynucleotide sequence, several modifications as indicated above may be present in combination.

The term "solid substrate" as used here includes all materials on which a nucleic acid fragment can be immobilized for utilization in methods calling for hybridization (particularly diagnostic tests), in affinity chromatography, and in separation processes. The solid substrate may be comprised of natural or synthetic materials, porous or nonporous, magnetic or nonmagnetic, or chemically modified or not, particularly polysaccharides such as cellulose-based materials, for example paper; cellulose derivatives such as cellulose acetate and nitrocellulose, polymers such as polyvinyl chloride, polyethylene, polystyrene, polyacrylates, or copolymers such as copolymers of vinyl chloride and propylene, vinyl chloride and vinyl acetate, etc.; polymers of the poly(N-isopropylacrylamide) (abbreviated NIPPAM) type; copolymers based on styrene or substituted styrenes; natural fibers such as cotton and synthetic fibers such as nylon; ceramics; silica. The solid substrates according to the invention can be for example in the form of a microtitration plate, a sheet, a cone, a tube, a well, a ball, or the like.

The term "hybridization" designates the formation of duplexes between nucleotide sequences that are sufficiently complementary by pairing bases of the Watson and Crick type or the Hoogsteen type (Thuong N.T., *Angew. Chem. Int. Ed., Engl.*, 32:666–690, 1993).

The term "oligonucleotide" designates a single-stranded sequence composed of nucleotides which may be deoxyribonucleotides or ribonucleotides; these nucleotides can be modified as described above in the paragraph relating to the description of the terms "nucleic acid fragment" or the like.

The term "chimera oligonucleotide" designates an oligonucleotide composed of at least two different varieties of nucleic sequences, which differ from each other by their chemical nature. One may for example cite chimera oligonucleotides containing at least one oligodeoxyribonucleotide sequence, or DNA-type, and at least one oligoribonucleotide sequence, or RNA-type.

The term "promoter sequence" or "promoter region" designates a 5' region of an oligonucleotide, particularly a chimera oligonucleotide as described in the present application, which has one of the strands of a promoter of an RNA polymerase, namely a sequence or structure that allows transcription to be initiated. Such sequences are well known. For example, one may cite natural RNA polymerase promoters, shortened sequences derived from natural promoters that have preserved their functionality, or "loop" structures capable of initiating transcription (Møllegaard N.E. et al., 1994, *Proc. Natl. Acad. Sci., USA*, 91:3892–3895).

"Sense sequence of an RNA polymerase promoter" designates the sequence of a promoter whose 3' end is located upstream of the transcription initiation site which is defined by this same promoter.

"Antisense sequence of an RNA polymerase promoter" designates the sequence of a promoter whose 5' end is located upstream of the transcription initiation site which is defined by this same promoter.

"Homologous sequence of another sequence" designates a sequence capable of hybridizing with a sequence that strictly complements said other sequence. The homologous sequence is either identical to said other sequence or sufficiently similar to hybridize with said strictly complementary sequence.

"Complementary sequence of another sequence" designates a sequence that can hybridize with said other sequence. A strictly complementary sequence of another is a sequence in which each of the bases can pair with a base of the other sequence without mismatching.

The expression "nucleic acid to be amplified" may designate either of the two complementary strands of a target nucleic acid, the number of copies of which is to be multiplied.

The term "initiation sequence" or "initiation region" designates a region of chimera oligonucleotides described in the present application which is between the promoter region located at the 5' end and the probe region located at the 3' end. The chemical nature of the initiation sequence permits a specific interaction either with the nucleic acid to be amplified or re-amplified or with its complementary sequence. The role of this initiation sequence is to allow, due to its chemical nature and its sequence that at least partially complements the nucleic acid to be amplified or reamplified, selective degradation of the target sequence and/or the sequence complementing the target sequence in the target sequence/initiation duplex and/or the target sequence complementing sequence/initiation sequence duplex, respectively, particularly by digestion by RNase H if the target sequence is an RNA. Also, the initiation sequence encloses the transcription initiation site. The transcripts generated under the influence of the promoter region will have, at 5', a sequence which complements at least part of the initiation sequence and whose length is a function of the location of the transcription initiation site on the initiation sequence.

The term "probe sequence" or "probe region" designates a region of the chimera oligonucleotides described in the present application, which region is located at the 3' end relative to the initiation region. The chemical nature of the probe sequence allows hybridization of the chimera oligonucleotide specifically and stably on the nucleic acid to be amplified or reamplified, particularly when the latter is of a ribonucleic nature, by formation of a duplex insensitive to the degradation activity referred to in the preceding definition. Moreover, the 3' end of this probe sequence will necessarily be blocked to prevent its being elongated by a polymerase.

The term "duplex" designates a double-stranded nucleic acid/nucleic acid hybridization product, it being understood that either of these nucleic acids can include at least one chemical modification.

The term "heteroduplex" designates an RNA-DNA hybrid. The term "homoduplex" designates a DNA-DNA hybrid or an RNA-RNA hybrid.

The term "triphosphate nucleosides" designates either triphosphate deoxyribonucleosides and/or triphosphate ribonucleosides, both of which may be modified.

In the present application, the term "upstream" designates a region located at the 5' end of the nucleic acid or the polynucleotide sequence in question, and the expression "downstream" designates a region at the 3' end of said nucleic acid or said polynucleotide sequence.

Position +1 designates the transcription initiation site. The template nucleotide at +1 is the first copied nucleotide and is at position 5' of the newly synthesized RNA.

The noun "transcript" designates a transcription product, namely an RNA newly synthesized at the time the template was transcribed under the dependence of the promoter that initiated the transcription.

An oligonucleotide "blocked at 3'" is a nucleotide that, in end region 3', has a modification that prevents it being elongated by a polymerase. The oligonucleotide blocked at 3' can for example have a terminal nucleotide 3' that has no 3'-OH group, particularly by incorporation of a nucleoside such as deoxy-3'-adenosine (or cordycepine). One may also block the 3' end by substituting the hydrogen in the 3-OH group for example with the aid of an alkyl or aryl group, in a manner known of itself. Blocking at 3' can also be achieved by the presence at the 3' end of one or more nucleotides which cannot pair with the template-target, particularly by choosing one or more nucleotides that do not complement the target for the 3' end.

An oligonucleotide sequence is called "DNA type" if it is comprised of DNA or if it is a modified polynucleotide sequence that, in addition to the nucleic acid strand hybridization properties, has at least one other property in common with the DNA. This common property will of course depend on the functionality of the modified sequence: It is in the exercise of this functionality that the sequence in question has a property in common with the DNA (namely behaves like a DNA). For example, the promoter sequence defined above can be a modified sequence which, in the form of a double strand, is capable of functioning as an RNA polymerase promoter like classical promoters comprised of double-stranded DNA: In this case, such a sequence is said to be of the DNA type. Likewise, the initiation sequence defined above can be a modified sequence which can hybridize with part of the target and, when hybridized with part of the target, allows degradation of this part of the target (just as a DNA hybridized with an RNA allows degradation of the hybridized part of the RNA under the action of an RNase H).

An oligonucleotide sequence is called "RNA type" if it is composed of RNA or if it is a modified polynucleotide sequence that, in addition to nucleic acid strand hybridization properties, has at least one other property in common with the RNA. This common property of course depends on the functionality of the modified sequence in question. For example, the probe sequence defined above can be a modified probe capable of hybridizing with the target and, when it is hybridized with a part of the target constituted of RNA, allows (like an RNA sequence and contrary to a DNA sequence) degradation of this part of the target under the action of an RNase to be avoided.

"Defined end" of a nucleic acid means an end with a known sequence. This end can be natural or obtained by chemical, physical, or enzymatic modification.

Hence the present invention relates to a chimera oligonucleotide that can in particular be used in the process of amplifying a target sequence of a nucleic acid, said target sequence having, at its 3' end, a downstream sequence, said chimera oligonucleotide having successively, from its 5' end to its 3' end:

a first oligonucleotide segment of the DNA type comprising a sense sequence of a promoter of an RNA polymerase, a second oligonucleotide segment, of the DNA type, comprising the transcription initiation site for said promoter, at least the 3' region of said second segment being capable of hybridizing with at least part of said downstream sequence, and a third oligonucleotide segment, of the RNA type, of which at least the region comprising the 5' end of said third segment is capable of hybridizing with a part of the target sequence contiguous to the part of said downstream sequence which is capable of hybridizing with said second segment, said third segment being blocked at 3'.

In general, the second and third segments of the oligonucleotide can each contain 2 to 30 nucleotides, in particular 4 to 20 nucleotides.

As will be seen below in the detailed description of the invention, a chimera oligonucleotide as defined above allows transcripts to be obtained easily from a DNA or RNA target sequence.

By using two chimera oligonucleotides as defined below, one capable of hybridizing with a target sequence and the other capable of hybridizing with a sequence complementing said target sequence, it is possible to achieve cyclic amplification of the target sequence and its complementary sequence, and the invention also relates to a set of oligonucleotides for obtaining transcripts, or for cyclic amplification with transcripts being obtained, of a target sequence of a nucleic acid and/or its complementary sequence, said set comprising:

a first chimera oligonucleotide as defined above, capable of hybridizing with a downstream region of the target sequence, and a second chimera oligonucleotide as defined above capable of hybridizing with a downstream region of a nucleotide sequence complementing said target sequence.

The chimera oligonucleotides of the invention can be synthesized by known methods; see for example Sinha et al., Biochimie, 75, 13–23 (1993).

The invention also relates to a process for obtaining transcripts, or cyclic amplification with transcripts obtained, of a target sequence of a nucleic acid and/or a sequence complementing said target sequence, said target sequence having at its 5' end an upstream sequence and at its 3' end a downstream sequence, said process comprising, under conditions allowing hybridization and functioning of the enzyme activities present, the bringing into contact of a sample containing or possibly containing said nucleic acid, with:

a) a first chimera oligonucleotide as defined above, capable of hybridizing with the downstream sequence of the target sequence, b) possibly a second chimera oligonucleotide as defined above, capable of hybridizing with a downstream region of a sequence complementing said target sequence, said downstream region complementing said upstream sequence, c) and an enzyme system containing a DNA polymerase activity, an RNA polymerase activity capable of functioning with said promoter, and an activity able specifically to degrade the region of the target or of the complementary of the target which is capable of pairing with at least part of the second segment of the first or second oligonucleotide, respectively, and incubation of the mixture obtained for a sufficient length of time.

The upstream and downstream sequences are non-overlapping sequences. Usually the upstream and downstream sequences are not identical.

The process according to the invention is implemented under conditions allowing hybridization of the oligonucleotides with their target strands and functioning of the various enzyme activities involved. These conditions are well known and will not be repeated in detail here. Of course, appropriate buffer solutions are used in the presence of excess triphosphate ribonucleosides and triphosphate deoxyribonucleosides necessary in particular for elongating the DNA and synthesizing the transcription products.

The amplification reaction can also be conducted on a solid substrate. Fixation of the chimera oligonucleotide that carries a probe sequence hybridizing with the starting nucleic acid molecule allows a step in which the target is purified prior to the amplification step and allows detection, on the solid substrate, of only the amplification products that have a sequence homologous to the target. Fixation of the two chimera oligonucleotides allows detection, on the solid substrate, of all the amplification products: those with a sequence homologous to the target and those with a sequence complementing the target.

The process according to the invention can be conducted isothermally. Those skilled in the art will easily understand that it is, however, possible to implement this process using temperature cycles that may favor one enzyme activity at the expense of another to favor, where applicable, a precise order in the successive functioning of the various enzyme activities involved.

According to one particular embodiment, said specific degradation activity of the target is an RNase H activity. It must be understood that in the case the starting nucleic acid is a DNA, the target sequence degradation activity by RNase H is conducted on the (RNA) transcripts obtained according to the process of the invention and not on the starting DNA.

The process of the invention can be implemented by introducing from the outset, in a reaction enclosure, all the ingredients necessary for proper conduct of the process, so that contamination can be avoided.

Of course, the process according to the invention can involve prior stages such as extraction of nucleic acids from a biological sample or denaturation of the starting nucleic acid molecule to obtain a single-stranded structure if the starting nucleic acid is a duplex or if it is a highly structured molecule.

Likewise, the process according to the invention can be followed for example by stages of separation and/or quantification of the transcription products or amplification products, which stages can be implemented in a manner known of itself.

The invention also relates to a device for detecting a target nucleic acid which may be present in a sample, said device allowing the amplification method described above to be implemented.

The invention will now be described in greater detail with reference to the attached drawing wherein the single figure schematically describes a particular embodiment of the process of the invention, comprising the obtaining of nucleic acid sequences with defined ends that can be part of the amplification reaction cycle also called "Amplification using a Promoter Chimera" (abbreviated APC) subject of the invention.

Figure 1:
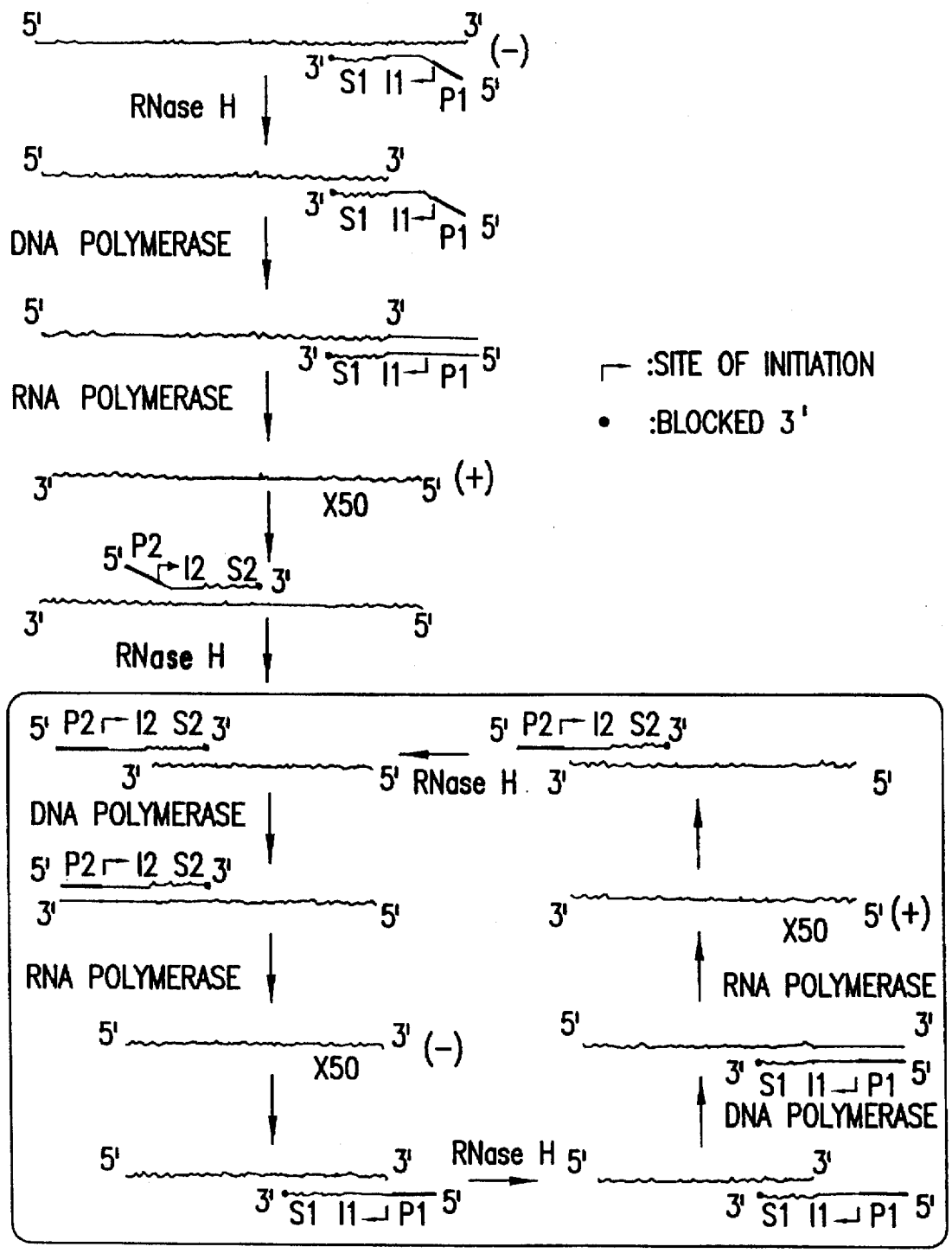
FIG. 1 shows transcription and amplification by a chimera oligonucleotide hybridizing to a target RNA molecule.

The wavy lines represent nucleic acids with a ribonucleic nature. The fine lines represent nucleic acids with a deoxyribonucleic nature. The thick lines represent sequences of deoxyribonucleic acid constituting one of the strands of a sequence able to play the role of a promoter. The two chimera oligonucleotides are each comprised of a deoxyribonucleic acid sequence ($P_1$ or $P_2$) that can play the role of RNA polymerase promoter sense strand, of a transcription initiation deoxyribonucleic sequence ($I_1$ or $I_2$), and a probe ribonucleic sequence ($S_1$ or $S_2$). The chimera oligonucleotides are blocked at 3'. This block is represented by a black dot. The transcription initiation site, also called position +1, is represented by an arrow. Two nucleic acid strands shown in parallel side by side are hybridized. The "+" and "−" signs refer to sequences belonging to opposite strands of a nucleic acid, namely complementary strands.

DETAILED DESCRIPTION OF THE INVENTION

As can easily be seen from FIG. 1, depending on whether one or two chimera oligonucleotides are used, the process of the invention comes down to being either a transcript-obtaining process or a process of cyclic amplification with production of transcripts.

According to the diagram in FIG. 1, the first chimera oligonucleotide (with sequences $P_1$, $I_1$, $S_1$) is hybridized on a beginning ribonucleic molecule by means of the probe sequence of ribonucleic nature ($S_1$) and all or part of the initiation sequence of deoxyribonucleic nature ($I_1$). Degradation of the RNA in the RNA:DNA heteroduplex region formed by hybridization of the beginning RNA molecule with all or part of the DNA initiation sequence ($I_1$) allows an end 3' to be created on the beginning molecule and the end 3' of the target sequence thus to be defined, if it had not already been defined. Preferably, the RNA of the RNA:DNA heteroduplex region is degraded by RNase H activity. However, this degradation can be effected by any other means. The $I_1$ region which is hybridized with the target sequence is, as far as possible, a sequence adapted to digestion by the RNase H used. In particular, this region must be long enough to serve as a substrate for this enzyme and preferably have the bases most favorable for the reaction. According to Keller et al. (1979, *Nucleic Acid Research*, 7:179–192), a sequence of four nucleotides will be sufficient to serve as a substrate for RNase H. If the beginning molecule is DNA and the RNase H is present initially, the initiation sequence should, by means of its size in particular, allow stable hybridization of the chimera oligonucleotide on the beginning nucleic acid. The RNase H activity may be carried by different enzymes, as for example the *E. coli* RNase H, or be associated with a reverse transcriptase such as the AMV (avian myeloblastosis virus) reverse transcriptase.

The first chimera oligonucleotide remains a hybrid with the beginning RNA molecule because RNase H does not degrade the RNA:RNA homoduplex (nor the single-stranded RNAs). The $S_1$ probe sequence is long enough to allow stable hybridization by itself. The length of this probe sequence also guarantees the specificity of the system: Just one nucleic acid with a sequence hybridizing specifically with the chimera will be amplified. The probe sequence will preferably have at least five nucleotides. However, the stability of hybridization can also be improved by using modified nucleotides.

A DNA-dependent DNA polymerase capable of using an RNA primer allows the RNA to be elongated from the released 3' end and the antisense strand of the promoter to be synthesized. Appropriate DNA polymerases are in particular those which play a role in the replication cycle (as for example *P. polycephalum* alpha DNA polymerase or human placenta alpha DNA polymerase. However, DNA repair polymerase (such as the Klenow fragment of *E. coli* DNA polymerase 1 or *P. polycephalum* b-like DNA polymerase) also accept RNA primers (Nevinsky et al., 1990, *Biochemistry*, 29:1200–1207). The Klenow fragment of exo (−) *E. coli* DNA polymerase 1 (devoid of 3'-5' exonuclease activity), bacteriophage T7 DNA polymerase "SEQUENASE" or reverse transcriptases (AMV or MMLV) can also be used. Since the 3' end of the probe-promoter chimera oligonucleotide is blocked, there is no elongation by the DNA polymerase. Various blocking modes can be envisaged, as indicated in the "definitions" above.

Synthesis of the antisense strand of the promoter allows recognition of the promoter by an RNA polymerase specific to this promoter, for example a phage RNA polymerase. When the promoter is in the double-stranded form, transcription with the appropriate RNA polymerase becomes possible. The double-stranded promoter can for example have the sequence of a promoter for T3, T7, SP6, BA14, or K11 RNA polymerase, or a derived sequence that has preserved a promoter functionality for these RNA polymerases. For example, a specific sequence for T3 RNA polymerase is used as the SEQ ID No. 1 consensus sequence, a specific promoter sequence for T7 RNA polymerase as the SEQ ID No. 2 consensus sequence, a specific sequence for SP6 RNA polymerase as the SEQ ID No. 3 consensus sequence, a specific sequence for K11 RNA polymerase as the SEQ ID No. 4 consensus sequence, or a specific sequence for BA14 RNA polymerase as the SEQ ID No. 5 consensus sequence. Also, when two chimera oligonucleotides are used, the promoter sequences of the first and second chimera oligonucleotides may be specific to two different RNA polymerases.

DNA-dependent RNA polymerase activity is amply described in the literature for the phage RNA polymerases cited above. However, the invention may require transcription on a template of a ribonucleic nature and hence an RNA-dependent RNA polymerase activity initiated specifically by the promoter. Such an activity has been described for T3 RNA polymerase (Leary et al., 1991, *Gene*, 106:93–96, described in European Patent Application No. 369,775). In the invention described in European Patent No. 369,775, the amplification reaction is based on RNA-dependent RNA polymerase activity with initiation of transcription on a ribonucleotide on the template strand in the +1 position, with transcription occurring on a fully RNA template. However, the yield of this reaction is low. Transcription leads to synthesis of about or less than one transcript for 10 templates. It has now been discovered that this amplification rate can advantageously be increased when initiation of transcription by RNA-dependent RNA polymerase (for example T3 RNA polymerase, T7 RNA polymerase, or SP6 RNA polymerase) begins with a deoxyribonucleotide on the antisense strand (position +1) and transcription occurs first on a DNA matrix complementing initiation sequence I then on an RNA template. Under these conditions, transcription leads to at least 50 transcripts per template. According to the invention, the "initiation sequence $I_1$" (or $I_2$) region is present in the RNA form in the transcription product which will in turn become a target for the cyclic amplification reaction. Construction of chimera oligonucleotides makes possible specific digestion (in the complementary region of the initiation sequence in particular) by RNase H, of part of the RNAs to be amplified or re-amplified after hybridization of the chimera oligonucleotide, thus allowing synthesis of a complementary template DNA sequence of this same initiation sequence. This allows initiation region I to be obtained in the form of a DNA-DNA homoduplex and transcription to be initiated by RNA-dependent RNA polymerase on a DNA template strand, with transcription continuing only from the region complementary to probe sequence S on an RNA template. The length of the initiation sequence will for example be between 4 and 18 nucleotides.

Transcription by RNA polymerase allows multiple transcripts to be synthesized. These transcripts include a sequence fully complementary to that of the beginning nucleic acid except for their 5' end which was defined by the target RNA being cut by RNase H on the hybridized region at initiation region $I_1$ on the chimera oligonucleotide. Thus, if the chimera oligonucleotide has hybridized completely at the 3' end of the beginning nucleic acid, and if initiation sequence $I_1$ has only bases that strictly complement those of this target, the 5' end of the transcripts complements the 3' end of the beginning nucleic acid. On the other hand, if the chimera oligonucleotide has not hybridized strictly at the 3' end of the beginning molecule, the transcripts will be shorter than this beginning molecule. In all cases, the 5' end of the neotranscripts will be defined since this sequence will necessarily be homologous to that of the $I_1$ and $S_1$ regions of the chimera oligonucleotide.

According to one particular embodiment, initiation region $I_1$ can contain, in its 5' part, nucleotides not paired with the beginning molecule. As a result, the 5' end of the neotranscripts contains a sequence that does not completely complement that of this target and which can be chosen arbitrarily. Advantage can be taken of this choice option to favor increasing the transcription factor for example, particularly by choosing the consensus sequence of specific initiation of the transcription for the promoter and the enzyme that are used. For example, for T3 RNA polymerase, T7 RNA polymerase, and K11 RNA polymerase, this sequence will preferably be the SEQ ID No. 6 sequence; for SP6 RNA polymerase, this sequence will preferably be the SEQ ID No. 7 sequence; for BA14 RNA polymerase, this sequence will preferably be the SEQ ID No. 8 sequence. The choice of this part of $I_1$ that does not complement the target may also for example allow stabilization of the transcript or contribution of a particular sequence permitting detection.

The neotranscripts that come from transcription under the control of the promoter present in the $P_1$ segment can hybridize with the second chimera oligonucleotide by the intermediary of probe sequence ($S_2$) and by the intermediary of all or part of initiation sequence ($I_2$). This second chimera oligonucleotide has the same characteristics as the first promoter-probe chimera oligonucleotide described above, except for the fact that it is capable of hybridizing not with the downstream sequence of the beginning target but with an upstream sequence of the complement of the target (said downstream sequence of the complement being the complement of the upstream sequence of the beginning target). Preferably it has the same promoter sequence as the first promoter-probe chimera oligonucleotide. Once again, the RNA part of the RNA:DNA heteroduplex region formed by hybridization of the RNA transcripts with all or part of the DNA ($I_2$) type initiation sequence is degraded, for example, by digestion by RNase H. As indicated above, initiation region $I_2$ can include, at the 5' end, a sequence not hybridized with the transcripts. If the probe sequence $S_2$ is sufficiently long or hybridization is sufficiently stable, the transcripts remain hybridized with the second chimera oligonucleotide. An appropriate DNA-dependent DNA polymerase then allows synthesis of the antisense strand of the promoter by elongation of the transcripts along the chimera oligonucleotide. Preferably, the same DNA polymerase is used for installation of the second strand of the promoters of the first and second chimera oligonucleotides. Transcription with the appropriate RNA polymerase once again allows synthesis of multiple transcripts.

At their 3' ends, these transcripts carry the complementary sequences of $I_1$ and $S_1$ allowing hybridization with the first chimera oligonucleotide ($P_1$, $I_1$ $S_1$). The RNA strand of the new DNA:RNA heteroduplex formed, namely the region of the transcript complementary to region $I_1$, is the substrate of RNase H. Elongation of the 3' end of the transcript, with the aid of a DNA polymerase, will then form the antisense strand of promoter P1. An RNA polymerase specific to promoter $P_1$ then allows synthesis of multiple transcripts which, at their 3' end, have a complementary sequence of regions $I_1$ and $S_2$ of the second chimera oligonucleotide, allowing hybridization therewith. The RNA strand of this new DNA:RNA hybrid can be degraded, in its complementary region with region $I_2$, by RNase H. The cycle can then be reiterated.

Because of repetition of chimera oligonucleotide installation on a ribonucleic acid sequence, the method according to the invention leads to synthesis of multiple transcripts, and allows the initial target nucleic acid fragment to be amplified exponentially.

It can easily be seen that for the method of the invention to function with a DNA target, it is necessary for the 3' end of this DNA to be defined. In other words, in this case, the downstream sequence of the target sequence corresponds to the 3' end sequence of the beginning DNA. This can be done in known fashion in operations preceding implementation of the process of the invention. To define one end on a double-stranded DNA, one can cut the target with restriction enzymes. If the DNA is single-stranded, one can hybridize oligodeoxyribonucleotides at the point to be cut, allowing cutting by restriction enzymes. One can also define the 3' end using a blocker: On a single-stranded DNA, one may hybridize two oligonucleotides on regions that must become the ends. The upstream oligonucleotide is subjected to enzyme elongation. When the enzyme arrives at the downstream oligonucleotide, called blocker oligonucleotide, the elongation reaction is stopped. This stoppage may be brought about by different factors; in particular, a polymerase bereft of displacement activity can be used, and this will be blocked by an oligonucleotide comprised of natural bases. If the polymerase has displacement activity, the blocker oligonucleotide can have chemical modifications inducing blocking (for example psoralene) or modifications at the internucleotide bond (as for example phosphorothioate, H-phosphonate, or alkyl phosphonate bonds) or at the skeleton, for example alpha-oligonucleotides (French Patent No. 2,607,507) or PNAs (Egholm et al., 1992, *J. Am. Chem. Soc.*, 114:1895–1897). Another method consists of using an initiation sequence I comprising a restriction site present on the target sequence, which site contains modified nucleotides whose nature does not allow cutting by the restriction enzyme. Thus, a 3' end defined on a DNA target is obtained by selective restriction of the target strand.

The following examples illustrate the invention. Unless stated to the contrary, the methods relating to implementation of the examples described below conform to their description by Sambrook et al. (1989, *Molecular Cloning:* A Laboratory Manual, 2nd Edition, Cold Spring Harbor Laboratory, Cold Spring Harbor).

The tests were performed on the sequence of the TEM gene coding for a β-lactamase inducing resistance to ampicillin and present in particular in the pBR322 plasmid.

In general, the reactions described below were conducted in a final volume of 20 µl of buffer: 40 mM Tris-HCl pH 8.1, 10 mM MgCl$_2$, 1 mM NTP, 1 mM dNTP, 5 mM DTT, 1 mM spermidine-HCl, 8% polyethylene glycol, 0.01% triton X100, 50 µg/ml bovine serum albumin; however, some of these parameters can be adjusted for each of the protocols. The enzymes used are T7 RNA polymerase ("OZYME-BIOLABS"), T3 RNA polymerase (pharmacia), SP6 RNA polymerase ("PHARMACIA"), "KLENOW sequencing GRADE" (commercial name; "BOEHRINGER"), Klenow exo(-) (USB), reverse transcriptase "SUPERSCRIPT II" ("GIBCO BRL"), "SEQUENASE" (commercial name; USB), *E. coli* RNase H ("BOEHRINGER").

NTP and dNTP designate triphosphate nucleosides.

In general, no prior optimization experiments were done on the reaction conditions.

EXAMPLE 1

Synthesis of DNA/RNA chimera oligonucleotides

The chimera oligonucleotides T7(+)-A27-RNAA28(SEQ ID No. 30 and 43) and T7(+)-A21-RNAA20(SEQ ID Nos. 29 and 42) are prepared on a DNA/RNA "APPLIED BIOSYSTEMS" 394 synthesizer. Synthesis goes from 3' to 5' using phosphoramidite chemistry. The RNA part is done with ribonucleotides furnished by the "APPLIED" company. They are applied at 2' by a t-butyldimethylsilyl (t-BDMS) group (Admf: ref. No. 401350, Gdmf: ref. No. 401351, Cibu: ref. No. 401352, and U: ref. No. 401353). Since the RNA part is located at 3', chimera synthesis begins with a substrate bearing a ribonucleotide. The synthesis substrates are RNA columns, 1 μmol 1000 A, adenosine-WPS from "BIOGENEX" (ref. No. 8310-1).

The DNA part is done with rapid deprotection deoxyribonucleotides from "PHARMACIA" (PAC dA: ref. No. 27-1723-03, iPr-PAC dG: ref. No. 27-1726-03, IBU dC: ref. No. 27-1725-03). The T deoxyribonucleoside comes from "APPLIED BIOSYSTEMS" (ref. No. 400329).

The two synthesis cycles used conform to the manufacturer's instructions.

An ammonia solution in anhydrous ethanol is used to restrict the chimera of the substrate. The solution is obtained by bubbling anhydrous ammonia ("ALDRICH" ref.No. 29, 499-3) in pure ethanol ("MERCK" ref. No. 983) for 1 h.

Deprotection of the chimera oligonucleotide, with the exception of the hydroxyl groups at 2' of the RNA part, is carried out in this same ammonia solution overnight at room temperature.

After evaporating off the ammonia solution in the rotary evaporator, 50 equivalents of tetrabutylammonium fluoride (TBAF 1, 1 M/THF, "ALDRICH" 21, 614–3) are used to deprotect the hydroxyl groups at 2'. After 24 h contact at room temperature with TBAF, the chimera is dried in the rotary evaporator then placed in 1 ml of sterile "MILLI" Q water. The aqueous solution is washed with ethyl acetate and desalted on an ion exchange column under the following conditions:

Column: "WATERS" protein-pak DEAE 15HR

15 μm, 1000 A

AP-1 10*100 mm

Buffers:

A=TEAB 0.1M (TEAB=triethylamine bicarbonate)
B=TEAB 2M

The product is loaded into the column with 100% buffer A for 20 min then eluted with 100% buffer B for 30 min at a rate of 4 ml/min.

Buffer B is made by bubbling carbon dioxide ("ALDRICH" ref. No. 29, 510-8) in a mixture of triethylamine ("ALDRICH" ref. No. 23, 962-3) and sterile water.

After desalting, the chimera molecule is dried in the rotary evaporator then added to 1 ml of sterile water. The chimera is then purified by reversed-phase chromatography under the following conditions.

Preparation column on Ultrapore RPMC Beckman dp 5 μm, 10*250 mm Serial No. 238770

Buffers:

A=TEAA 0.1M
B=TEAA 0.1M/CH$_3$CN 50%

References: Triethylammonium acetate (TEAA) 2M HPLC grade, "APPLIED BIOSYSTEMS" Acetonitrile: Baker HPLC gradient grade Gradient: 20–30% of B for 10 min, then 30–70% of B for 20 min at a rate of 4.7 ml/min.

EXAMPLE 2

Elongation of an RNA primer on a DNA template

The purpose of this example is to show that an RNA primer can serve as a substrate for a DNA polymerase with a view to its elongation on a DNA template. For this purpose, several oligonucleotides were used. Oligonucleotide T7(+)-A27-A28 (SEQ ID No. 11) constitutes the DNA matrix and, from its 5' end to its 3' end, carries the sense sequence of promoter T7, an A27 sequence, and an A28 sequence. Oligonucleotide RNAA19 (SEQ ID No. 9) and oligonucleotide A19 (SEQ ID No. 10) are primers of an RNA nature and a DNA nature respectively whose sequences are complementary to the A28 probe sequence of oligonucleotide T7(+)-A27-A28 (SEQ ID No. 11). These two oligonucleotides are radiolabeled with $^{32}$p at their 5'-OH end by the polynucleotide kinase.

Oligonucleotide T7(+)-A27-A28 (SEQ ID No. 11) and oligonucleotide RNA19 (SEQ ID No. 9) or A19 (SEQ ID No. 10) are incubated for 5 min at 650° C. at the concentration of 5·10$^{10}$ copies/μl each in a final volume of 20 μl of the reaction medium as described above, adjusted to 20 mM MgCl$_2$ and in the absence of NTP. The tubes are then left to stand for 10 min at room temperature to allow hybridization of the oligonucleotides then preincubated for about 1 min at 370° C. before the addition of 13 units of "SEQUENASE" or 10 units of Klenow or 130 units of "SUPERSCRIPT II" reverse transcriptase. The reaction controls are done in parallel without enzyme and/or without template. After incubation for 1 h at 370° C., the reactions are stopped by cooling over ice. Part of each sample (10 μl) is mixed with 10 μl formamide blue (90% formamide, 0.02% xylene cyanole, 0.02% bromophenol blue, 25 mM EDTA) then analyzed by electrophoresis on gel (15% polyacrylamide, 7M urea) in the presence of a molecular-weight marker formed by an oligodeoxyribonucleotide mixture of 60, 55, 50, 45, 35, 30, and 25 nucleotides. After drying, the gel is autoradiographed on X-ray film.

Whatever the enzyme used, equivalent elongation is observed from a DNA primer and from an RNA primer. In the case of elongation by "SEQUENASE", however, the presence of longer-than-expected extension products is noted (50 nucleotides).

EXAMPLE 3

Transcription by T7 RNA polymerase, T3 RNA polymerase, and SP6 RNA polymerase on single template or double strand of an entirely DNA or RNA nature from the +18 position. Effect of exogenous DNA.

The activities of T3 RNA polymerase, SP6 RNA polymerase, and T7 RNA polymerase were tested on different types of templates. For this purpose, an oligonucleotide series was constructed (composition is indicated from 5' to 3' with the 5' end on the left):

for analysis of transcription by T3 RNA polymerase:

oligonucleotide T3(−)-A18-A19 (SEQ ID No. 19): the antisense sequence of promoter T3, an A18 sequence of a DNA nature, and an A19 sequence of a DNA nature, oligonucleotide T3 (+) -A27-A28 (SEQ ID No. 15): the sense sequence of promoter T3, an A27 initiation sequence of a DNA nature, and an A28 probe sequence of a DNA nature, oligonucleotide T3(+) (SEQ ID No. 16): the sense sequence of promoter T3, chimera oligonucleotide T3(−)-A18-RNAA19 (SEQ ID Nos. 20 and 21): the antisense sequence of promoter T3, an A18 sequence of a DNA nature, and an A19 sequence of an RNA nature, for analysis of transcription by SP6 RNA polymerase:

oligonucleotide SP6(−)-A18-A19 (SEQ ID No. 17): the antisense sequence of promoter SP6, an A18 sequence of a DNA nature, and an A19 sequence of a DNA nature, oligonucleotide SP6(+) -A27-A28 (SEQ ID No. 13): the sense sequence of promoter SP6, an A27 initiation sequence of a DNA nature, and an A28 probe sequence of a DNA nature, oligonucleotide SP6(+) (SEQ ID No. 14): the sense sequence of promoter SP6, chimera oligonucleotide SP6(−)-A18-RNAA19 (SEQ ID Nos. 20 and 40): the antisense sequence of promoter SP6, an A18 sequence of a DNA nature, and an A19 sequence of an RNA nature, for analysis of transcription by T7 RNA polymerase:

oligonucleotide T7(−)-A18-A19 (SEQ ID No. 18): the antisense sequence of promoter T7, an A18 sequence of a DNA nature, and an A19 sequence of a DNA nature, oligonucleotide T7(+)-A27-A28 (SEQ ID No. 11: the sense sequence of promoter T7, an A27 initiation sequence of a DNA nature, and an A28 probe sequence of a DNA nature, oligonucleotide T7(+) (SEQ ID No. 12): the sense sequence of promoter T7, chimera oligonucleotide T7(−)-A18-RNAA19 (SEQ ID Nos. 20 and 22): the antisense sequence of promoter T7, an A18 sequence of a DNA nature, and an A19 sequence of an RNA nature.

For studying the activity of T3 RNA polymerase on DNA matrix, the template oligonucleotide T3(−)-A18-A19 (SEQ ID No. 19) is hybridized either with the oligonucleotide T3(+)-A27-A28 (SEQ ID No. 15) for studying transcription on a double-stranded template; or with the oligonucleotide T3(+) (SEQ ID No. 16) for studying transcription on a single-stranded template; or the oligonucleotide T3(−)-A18-A19 (SEQ ID No. 19) is tested alone for studying transcription with a single-stranded promoter on a single-stranded template.

For studying the activity of T3 RNA polymerase on a template of a DNA nature from position +1 to position +17 and of an RNA nature from position +18 (positions relative to the transcription initiation site), the template oligonucleotide T3(−) -A18-RNAA19 (SEQ ID Nos. 20 and 21) is hybridized with the same nontemplate oligonucleotides as in the previous case.

Likewise, for studying the activity of SP6 RNA polymerase on a DNA template, the template oligonucleotide SP6(−)-A18-A19 (SEQ ID No. 17) is hybridized either with the oligonucleotide SP6(+)-A27-A28 (SEQ ID No. 13) for studying transcription on a double-stranded matrix; or with the oligonucleotide SP6(+) (SEQ ID No. 14) for studying transcription onto the single-stranded matrix; or the oligonucleotide SP6(−)-A18-A19 (SEQ ID No. 17) is tested alone for studying transcription with a single-stranded promoter and on a single-stranded template.

For studying the activity of SP6 RNA polymerase on a template of a DNA nature from position +1 to position +17 and of an RNA nature from position +18, the template oligonucleotide SP6(−)-A18-RNAA19 (SEQ ID Nos. 20 and 40) is hybridized with the same nontemplate oligonucleotides as in the preceding case. Finally, for studying the activity of T7 RNA polymerase on DNA template, the template oligonucleotide T7(−)-A18-A19 (SEQ ID No. 18) is hybridized either with the oligonucleotide T7(+)-A27-A28 (SEQ ID No. 11) for studying transcription on a double-stranded template; or with the oligonucleotide T7(+) (SEQ ID No. 12) for studying transcription on the single-stranded template; or the oligonucleotide T7(−)-A18-A19 (SEQ ID No. 18) is tested alone for studying transcription with a single-stranded promoter on a single-stranded template.

For studying the activity of T7 RNA polymerase on a template of a DNA nature from position +1 to position +17 and of an RNA nature from position +18, the template oligonucleotide T7(−)-A18-RNAA19 (SEQ ID Nos. 20 and 22) is hybridized with the same nontemplate oligonucleotides as in the preceding case.

In addition, the tests using T7 RNA polymerase were also conducted in the presence of 10 ng or 100 ng of salmon sperm DNA to test the effect of exogenous DNA on transcription.

In these tests, the oligonucleotides are at the concentration of $5 \cdot 10^9$ copies/µl each. The reactions are conducted in a final volume of 20 µl of the reaction medium described above, in the absence of dNTP, taking care to adjust the conditions according to the polymerase tested as indicated below: 10 mM $MgCl_2$ and 1 mM $CaCl_2$ for T3 RNA polymerase; 4 mM $MgCl_2$ for SP6 RNA polymerase, and 6 mM $MgCl_2$ for T7 RNA polymerase. The samples are denatured by heating at 650° C. for 5 min, then lowered to 370° C. taking 10 min. The transcription reaction is then primed by adding 50 units of polymerase and, after 2 h incubation at 370° C., the reaction is stopped on ice. The 10 µl samples are mixed with 10 µl formamide blue and analyzed by electrophoresis on gel (20% polyacrylamide, 7 M urea) followed by electrotransfer on "HYBOND N" "AMERSHAM"), hybridization with the oligonucleotide A19 (SEQ ID No. 10) labeled with peroxidase, and developed by a calorimetric substrate, diaminobenzidine.

It has been found that, whatever the enzyme used, the results of transcription on a DNA template are equivalent whether the template is in the double- or single-stranded form. On the other hand, the experimental conditions as described do not allow transcription from a single-stranded DNA promoter to a single-stranded DNA template. Likewise, no transcription is observed from a single-stranded DNA promoter on a single-stranded RNA template for any of the three enzymes.

The study of transcription by T3 RNA polymerase or by T7 RNA polymerase in the presence of a double-stranded DNA promoter on an RNA template from position +18 [oligonucleotides T3 or T7(−)-A18-RNAA19] shows that the rate of transcription obtained with this template in its double-stranded form is lower than that obtained on a DNA template (single- or double-stranded); on the other hand, the rate obtained with this same template in its single-stranded form is as high as that obtained on a DNA template. The results observed in the case of SP6 RNA polymerase show that the transcription rate on a single-or double-stranded RNA template is lower than that on a DNA template.

The study of the effect of the presence of salmon DNA on transcription by T7 RNA polymerase shows that the rate of this transcription is unaffected by the presence of exogenous DNA.

With the transcription factor defined as the number of transcripts obtained per template, this factor may be estimated at approximately 10 for transcription on double-stranded template and RNA starting at +18 for T3 RNA polymerase, at approximately 50 for transcription on single-stranded template, and RNA starting at +18 for the same enzyme. For SP6 RNA polymerase, the transcription factor on double-stranded or single-stranded template and RNA starting at +18 can be evaluated at approximately 10, for T7 RNA polymerase, the transcription factor on double-stranded template and RNA starting at +18 can be evaluated at approximately 50 and at approximately 100 on single strand.

EXAMPLE 4

Transcription on RNA template from position +1 by T3 RNA polymerase. Transcription on single—or double-stranded template.

The activity of T3 RNA polymerase was tested on a fully-RNA template. For this purpose, a chimera oligonucleotide T3(−)-RNAA18-RNAA19 (SEQ ID Nos. 23 and 41) was constructed, comprising from its 5' end to its 3' end the antisense DNA sequence of the promoter of T3 RNA polymerase, an RNAA18 sequence of an RNA nature, and an RNAA19 sequence of an RNA nature. This oligonucleotide is hybridized either with oligonucleotide T3(+) (SEQ ID No. 16) to test the activity on a single-stranded RNA template or with oligonucleotide T3(+)-A27-A28 (SEQ ID No. 15) to test the activity on a double-stranded template. The reactions are conducted in 20 µl of the reaction medium described above, in the absence of dNTP, adjusted to 10 mM $MgCl_2$, with each of the oligonucleotides present at the concentration of $5 \cdot 10^9$ copies/µl. The reactions were also tested in the presence of 10 glycerol or 3% glycerol. After incubation for 5 min at 650° C. then cooling to 370° C. taking 10 min, the reaction was primed by adding 50 units of T3 RNA polymerase. After incubation for 2 h at 370° C., the reactions were stopped on ice. An aliquot fraction (10 µl) of the reaction products on a double-stranded template were digested by DNase I. The reactions are analyzed by electrophoresis of an aliquot part of 10 µl on gel (20% polyacrylamide, 7M urea), electrotransfer on "HYBOND N", hybridization with the oligonucleotide A19 (SEQ ID No. 10) labeled with peroxidase, and development by a chemiluminescent substrate, luminol.

The same control test as in Example 3 was repeated here and showed that the analysis process using luminol as a substrate was sufficiently sensitive to reveal $5 \cdot 10^{10}$ copies of the nontemplate oligonucleotide T3(+)-A27-A28 (SEQ ID No. 15) present on the blots in the case of reactions on a double-stranded template. However, the transcript obtained is smaller in size. Moreover, digestion by DNase I eliminates the background noise due to this hybridization. The results show that transcription is obtained on an RNA matrix starting at +1 both with the double-stranded and the single-stranded forms, but that the rate of this transcription is low: about one transcript per 10 templates is obtained.

EXAMPLE 5

Reiteration of promoter installation process and transcription on RNA template To demonstrate the possibility of installing a promoter on an RNA, obtaining complementary transcripts, reiterating installation of the promoter on these transcripts, and obtaining complementary transcripts of the transcripts of the first reaction, a target oligonucleotide RNAA20-RNAA19 (SEQ ID No. 28) of a fully RNA nature was constructed.

This oligonucleotide was mixed with the oligonucleotides T7(+)-A27-A28 (SEQ ID No. 11) and T7(+) -A21-A20 (SEQ ID No. 28) at the concentration of $5 \cdot 10^{10}$ copies/µl each in 20 µl of the reaction medium described above. After denaturation for 5 min at 650° C., the tubes are incubated for 10 min at room temperature then 1 min at 370° C. before addition of 10 units of Klenow. Incubation lasts 30 min at 370° C. The enzyme is denatured for 10 min at 65° C. A further incubation is carried out for 10 min at room temperature to allow the oligonucleotides to hybridize. After 1 min of preincubation at 37° C., 50 units of T7 RNA polymerase are added. Incubation lasts 1 h at 37° C. Certain reactions are stopped at this stage.

The reactions on which a second transcription stage is to be run are reheated at 65° C. for 10 min to denature the T7 RNA polymerase. After incubation at room temperature for 10 min, 10 units of Klenow are once again added and incubated at 37° C. for 30 min. After a new Klenow denaturation cycle (65° C., 10 min; room temperature, 10 min; preincubation at 37° C.), 50 units of T7 RNA polymerase are added and incubated 60 min at 370° C. The reactions are stopped in ice. One-fifth of the reaction product (representing $2 \cdot 10^{11}$ copies of each of the oligonucleotides initially present) is mixed with an equal volume of formamide blue and analyzed on gel (20% polyacrylamide, 7M urea). Various samples of the same reaction are analyzed in parallel. After electrotransfer on "HYBOND N", the blots are hybridized either with oligonucleotide A20 (SEQ ID No. 25) or with oligonucleotide A26 (SEQ ID No. 26) labeled with digoxigenin, developed by the "BOEHRINGER" detection system employing an immunoenzyme reaction with an antidigoxigenin antibody and a luminescent substrate, then autoradiographed by X-ray films.

In the first stage of transcription, the nontemplate oligonucleotide T7(+)-A27-A28 (SEQ ID No. 11) can hybridize onto the target RNAA20-RNAA19 (SEQ ID No. 24) because the A28 sequence is complementary to the A19 oligonucleotide. The second oligonucleotide T7(+)-A21-A20 (SEQ ID No. 28) which is present in the reaction plays no role. The Klenow extends the target RNA using oligonucleotide T7(+)-A27-A28 (SEQ ID No. 11) as a template. The T7 RNA polymerase can then recognize the promoter whose antisense strand has been formed and synthesize a transcript with a complementary sequence to the sequence of the RNA target. Oligonucleotide probe A20 (SEQ ID No. 25) allows these reaction products to be developed specifically.

In the second stage of transcription, the oligonucleotide T7(+)-A21-A20 (SEQ ID No. 28) hybridizes onto the 3' end of the products of the first reaction. The Klenow brings about elongation of the 3' end of these RNAs using the oligonucleotide T7(+)-A21-A20 (SEQ ID No. 28) as a template and thus forms the antisense strand of the promoter. The T7 RNA polymerase then synthesizes the complementary transcripts of the transcripts of the first stage. The oligonucleotide probe A26 (SEQ ID No. 26) allows these neotranscripts to be developed. The promoter T7(+)-A21-A20 is also revealed by the A26 probe; however, the expected transcripts have a size of 65 bases while this oligonucleotide has only 50 nucleotides.

The results obtained show that after a first transcription stage, transcripts of the expected size are obtained capable of hybridizing to probe A20. After the second transcription stage, a band corresponding to a molecular weight of approximately 80 bases appears while the band corresponding to the transcripts of the first stage decreases in intensity. This indicates that there is indeed an extension of transcripts from the first stage.

The results of hybridization with probe A26 show a band of the size of oligonucleotide T7(+)-A21-A20 (SEQ ID No. 28) present even in the absence of enzyme. The first transcription stage does not allow other bands hybridizing with A26 to appear. On the other hand, the second transcription stage causes bands with a higher molecular weight to appear, of which the majority band has electrophoretic migration corresponding to a product of the expected size.

Hence, these experiments show the possibility of reiterating installation of a promoter and transcription from a template formed by a neotranscribed RNA.

EXAMPLE 6
Installation of chimera oligonucleotide on RNA template and transcription reaction The target RNA corresponds to the sequence RNAA20-RNAA19-RNAA18 (SEQ ID 31). The chimera oligonucleotide used is T7(+)-A27-RNAA28 (SEQ ID Nos. 30 and 43). This chimera oligonucleotide contains, from 5' to 3':

- a first nucleic segment T7(+), of a DNA nature, corresponding to the sense sequence of a promoter for T7 RNA polymerase;
- a second nucleic segment A27, of a DNA nature, corresponding to an initiation sequence;
- and a third nucleic segment RNAA28, of an RNA nature, corresponding to a probe sequence.

It goes without saying that the A27 and RNAA28 segments of the chimera oligonucleotide are complementary to the RNAA18 and RNAA19 sequences of the RNA target, respectively. Moreover, blocking of the 3' end of the oligonucleotide is achieved by the presence of two 3'-terminal ribonucleotides which cannot pair with the target.

A reaction control is done with the target of an RNA nature RNAA20-RNAA19 (SEQ ID 24) which corresponds to the sequence of the target RNAA20-RNAA19-RNAA18 (SEQ ID 31) minus the sequence RNAA18, the substrate of RNase H in the chimera oligonucleotide hybrid T7(+)-A27-RNAA28/target RNAA20-RNAA19-RNAA18.

The reaction is conducted in the reaction medium described above in the presence of $5 \cdot 10^9$ copies/µl of chimera oligonucleotide and $5 \cdot 10^9$ copies/µl of target RNA in a final volume of 20 µl. To allow good hybridization at the start, the mixture is heated for 5 min at 650° C. then gradually cooled to 370° C. taking 10 min. After a brief preincubation at 370° C., one unit of RNase H is added and the mixture is held at 370° C. for 30 minutes. The RNase H is then denatured by incubation at 650° C. for 10 min. After gradual cooling to room temperature for 10 min, 10 units of exo(–) Klenow are added and incubation is carried out for 30 min at 370° C. The exo(–) Klenow enzyme is then denatured by heat and 50 units of T7 RNA polymerase are added. This is incubated for 60 min at 370° C. then the reactions are stopped by cooling on ice. Reaction controls are carried out: reactions with no enzyme, reactions without T7 RNA polymerase, without RNase H, or without exo(–) Klenow. Half the reaction volume of the samples is analyzed by electrophoresis on gel (polyacrylamide 20%, 7M urea) after mixing with formamide blue, electrotransfer on "HYBOND N", hybridization with oligonucleotide A19 (SEQ ID 10) labeled with peroxidase, and development by the calorimetric substrate (diaminobenzidine).

The results show that the expected transcripts are obtained whether the target RNAA20-RNAA19 (SEQ ID 24) or the target RNAA20-RNAA19-RNAA18 (SEQ ID 31) is used in the reactions employing the three enzymes. None of the reactions conducted in the absence of all the enzymes or one of the polymerases allows transcripts to be obtained. The reactions carried out without RNase H do not allow transcripts to be produced from the template RNAA20-RNAA19-RNAA18 (SEQ ID31) while the expected transcripts are obtained when the template RNAA20-RNAA19 (SEQ ID24) is used.

Analogously, production of transcripts can be shown by adding all the enzymes at the very beginning (after preincubation at 370° C. as stated above), then operating at a single temperature of 370° C.

EXAMPLE 7

The targets a re single-stranded RNA corresponding to the sequences SEQ ID 36 and SEQ ID 37, which complement each other (sense and antisense). These RNA strands are obtained by in vitro transcription of DNA fragments, obtained by PCR, which contain the promoter sequences specifically recognized by the T7 RNA polymerase. After transcription, the RNAs are purified on denaturing acrylamide gel.

The chimera oligonucleotides used, SEQ ID Nos. 34 and 44 and SEQ ID Nos. 35 and 45, contain, from 5' to 3':

- a first nucleic segment T7(+), of a DNA nature, corresponding to the sense sequence of a promoter for T7 RNA polymerase,
- a second nucleic segment, of a DNA nature, corresponding to an initiation sequence and complementing the 3' end of the target RNA,
- and a third nucleic segment, of a n RNA nature, complementing the target RNA.

The chimera oligonucleotide SEQ ID Nos. 34 and 44 partially complements the target SEQ ID 36, and the chimera oligonucleotide SEQ ID Nos. 35 and 45 partially complements the target SEQ ID 37.

The 3' end of these chimera oligonucleotides is blocked by the presence of one or two 3'-terminal ribonucleotides (a single ribonucleotide for SEQ ID Nos. 34 and 44) which cannot pair with the corresponding target.

Separate tests were conducted using the oligonucleotide SEQ ID Nos. 34 and 44 and the oligonucleotide SEQ ID Nos. 35 and 45 are primers, and the oligonucleotide SEQ ID 36 and oligonucleotide SEQ ID 37, respectively, as targets.

$5 \cdot 10^{10}$ copies/µl of chimera oligonucleotide and $5 \cdot 10^9$ copies/µl of target RNA are mixed in a final volume of 20 µl in the reaction medium as described in Example 6, to which 100 mM potassium glutamate are added. The mixture is heated for 5 minutes at 65° C., then cooled to 37° C. for 10 minutes. The enzymes are added in a single step in the form of a mixture of 1 unit heat-stable RNase H "HYBRIDASE" (Epicentre Technologies), 5 units Klenow, and 250 units T7 RNA polymerase. After incubation at 37° C. for 60 minutes, the reactions are stopped by cooling on ice. In parallel, reaction controls are carried out under identical conditions, either without enzyme or without target RNA. Half the reaction volume is analyzed by electrophoresis on gel (15% polyacrylamide, 7M urea) after mixing with formamide blue by electrotransfer on "HYBOND N" and by hybridizing with the oligonucleotide A21 (SEQ ID 38) or with the oligonucleotide A27 (SEQ ID 39) which are, respectively, specific to the transcripts from target RNA SEQ ID 36 or target RNA SEQ ID 37. The oligonucleotides used as detection probes are marked with peroxidase and developed by the colorimetric substrate DAB (diaminobenzidine).

The results show that the expected transcripts are obtained when either sense or antisense target RNA is used with the corresponding chimera oligonucleotide. None of the reactions carried out in the absence of enzymes or target RNA led to a transcript being obtained.

What is claimed is:

1. A chimeric oligonucleotide for amplifying a target sequence of a nucleic acid, said target sequence having a downstream sequence, said oligonucleotide having successively, from a first 5' end to a first 3' end:

a first oligonucleotide segment of the DNA type, said first segment comprising a sense sequence of a promoter of an RNA polymerase;

a second oligonucleotide segment of the DNA type, said second segment having a second 3' end and a 3' region comprising the second 3' end, and comprising a transcription initiation site for said promoter, at least said 3' region being one that hybridizes with at least a part of said downstream sequence; and a third oligonucleotide segment of the RNA type, said third segment comprising a third 5' end, a third 3' end and a 5' region comprising the third 5' end, at least said 5' region being one that hybridizes with a part of said target sequence contiguous to said at least a part of said downstream sequence, said third segment being blocked at said third 3' end.

2. An oligonucleotide according to claim 1, wherein the second segment includes 2 to 30 nucleotides.

3. An oligonucleotide according to claim 1, wherein the third segment includes 2 to 30 nucleotides.

4. An oligonucleotide according to claim 2, wherein the second segment includes 4 to 20 nucleotides.

5. Oligonucleotide according to claim 3, wherein the third segment includes 4 to 20 nucleotides.

6. A set of chimeric oligonucleotides for obtaining transcripts of at least one sequence selected from the group consisting of a target sequence of a nucleic acid and a complementary sequence that is complementary to said target sequence, said target sequence and said complementary sequence each having a downstream sequence, said set comprising:

first and second chimeric oligonucleotides, each having successively from a first 5' end to a first 3' end thereof:

a first oligonucleotide segment of the DNA type, comprising a sense sequence of a promoter of an RNA polymerase;

a second oligonucleotide segment of the DNA type, having a second 3' end and a 3' region including the second 3' end, and comprising a transcription initiation site for said promoter, at least the 3' region of said second segment of said first chimeric oligonucleotide being one that hybridizes with at least a part of said downstream sequence of said target sequence, and at least the 3' region of said second segment of said second chimeric oligonucleotide being one that hybridizes with at least a part of said downstream sequence of said complementary sequence; and a third oligonucleotide segment of the RNA type, having a third 5' end, a third 3' end and a 5' region comprising the third 5' end thereof, said third segment being blocked at the third 3' end, at least said 5' region of said third segment of said first chimeric oligonucleotide being one that hybridizes with a part of said target sequence contiguous to said at least a part of said downstream sequence of said target sequence, and at least said 5' region of said third segment of said second chimeric oligonucleotide being one that hybridizes with a part of said complementary sequence contiguous to said at least a part of said downstream sequence of said complementary sequence.

7. A process for obtaining transcripts of at least one nucleic acid sequence comprising a target sequence, said target sequence having an upstream sequence at a 5' end and a downstream sequence at a 3' end, said downstream sequence not overlapping said upstream sequence, said process comprising incubating for a sufficient time to obtain said transcripts, under conditions allowing hybridizing and functioning of enzyme activities, a mixture comprising:

a) a sample comprising said target sequence;

b) a first chimeric oligonucleotide according to claim 1, one that hybridizes with at least a part of the target sequence downstream sequence; and c) an enzyme system having a DNA polymerase activity, an RNA polymerase activity capable of functioning with said promoter, and a degrading activity capable of specifically degrading at least a part of a first degradable sequence consisting of said at least a part of said downstream sequence of the target sequence, said degrading activity being effective when said first degradable sequence is hybridized with at least said 3' region of said second segment.

8. A process according to claim 7, wherein said degrading activity is an RNase H activity.

9. The process according to claim 7, wherein said mixture further comprises a second chimeric oligonucleotide having successively from a first 5' end to a first 3' end thereof:

a first oligonucleotide segment of the DNA type, comprising a sense sequence of a promoter of an RNA polymerase;

a second oligonucleotide segment of the DNA type, having a second 3' end and a 3' region including the second 3' end, and comprising a transcription initiation site for said promoter, at least the 3' region of said second segment of said second chimeric oligonucleotide being one that hybridizes with at least a part of said downstream sequence of a complementary sequence complementary to said target sequence; and a third oligonucleotide segment of the RNA type, having a third 5' end, a third 3' end and a 5' region comprising the third 5' end thereof, said third segment being blocked at the third 3' end, at least said 5' region of said third segment of said second chimeric oligonucleotide one that hybridizes with a part of said complementary sequence contiguous to said at least a part of said downstream sequence of said complementary sequence, and wherein said degrading activity capable of specifically degrading at least a part of a second degradable sequence consisting of said at least a part of said downstream sequence of said complementary sequence, said degrading activity being effective when said second degradable sequence is hybridized with at least said 3'-region of said second segment of said second chimeric oligonucleotide.

* * * * *

UNITED STATES PATENT AND TRADEMARK OFFICE
CERTIFICATE OF CORRECTION

PATENT NO.   : 5,744,308
DATED        : April 28, 1998
INVENTOR(S)  : Francoise GUILLOU-BONNICI, Philippe CLEUZIAT, Francois MALLET, Pierre LEVASSEUR and William McALLISTER It is certified that error appears in the above-indentified patent and that said Letters Patent is hereby corrected as shown below:

Title page, in item [75], line 2, change "Lyons" to --Lyon--.

Signed and Sealed this

Fourteenth Day of July, 1998

*Attest:*

BRUCE LEHMAN

*Attesting Officer*      *Commissioner of Patents and Trademarks*